United States Patent [19]

Ricchiero et al.

[11] Patent Number: 5,607,864
[45] Date of Patent: Mar. 4, 1997

[54] FLUORESCENT LATICES HAVING VERY LOW DETECTION THRESHOLDS FOR FLUORESCENT EMISSION

[75] Inventors: Frederic Ricchiero, Montpellier; Joel Richard, Chantilly; Sophie Vaslin, Bry/Sur/Marne, all of France

[73] Assignee: Societe Prolabo, Paris Cedex, France

[21] Appl. No.: 319,782

[22] Filed: Oct. 7, 1994

Related U.S. Application Data

[63] Continuation-in-part of Ser. No. 43,748, Apr. 7, 1993, abandoned.

[30] Foreign Application Priority Data

Apr. 7, 1992 [FR] France ................... 92 04217

[51] Int. Cl.$^6$ ................... G01N 33/533
[52] U.S. Cl. ................... 436/533; 436/518; 436/531; 436/532; 436/534; 436/546; 436/800; 436/172; 252/301.16; 252/301.35; 252/408.1; 428/402
[58] Field of Search ................... 252/700, 301.16, 252/301.35, 408.1; 436/518, 528, 531, 533, 534, 532, 546, 800, 172; 422/82.07, 82.08; 428/402

[56] References Cited

U.S. PATENT DOCUMENTS 4,115,535  9/1978  Giaever ................... 436/533
4,127,499  11/1978  Chen et al. ................... 252/301.17

FOREIGN PATENT DOCUMENTS 0407188  1/1991  European Pat. Off. .

OTHER PUBLICATIONS

Vener et al., Analytical Biochemistry 198 pp. 308–311 (1991) "A novel Approach to Nonradioactive Hybridization assay of Nucleic Acids Using Stained Latex Particles".
Aldrich Catalogue, pp. 1179–1180 (1992) Aldrich Chemical Company, Milwaukee, WI, USA.
Hemmila, *Applications of fluorescence in immunoassays*, pp. 131–135 (1991) John Wiley & Sons, Inc.
Maeda, *Laser Dyes*, pp. 133–149 (1984) Academic Press, Inc.

*Primary Examiner*—Lora M. Green
*Attorney, Agent, or Firm*—Burns, Doane, Swecker & Mathis, L.L.P.

[57] ABSTRACT

Fluorescent latices, well suited for a wide variety of analytical techniques, comprise polymer particles having at least one hydrophobic fluorochrome encapsulated therein, notably at least one condensed polyaromatic compound or derivative thereof, or a tetraphenylporphine and/or organometallic complex thereof, and have a detection threshold for fluorescence which is less than or equal to $10^{-12}$ mol of particles per liter of latex.

23 Claims, No Drawings ated derivative thereof, or a tetraphenylporphine and/or one
FLUORESCENT LATICES HAVING VERY LOW DETECTION THRESHOLDS FOR FLUORESCENT EMISSION

CROSS-REFERENCE TO COMPANION APPLICATION

This application is a continuation-in-part of our earlier copending application, Ser. No. 08/043,748, filed Apr. 7, 1993 and assigned to the assignee hereof now abandoned.

BACKGROUND OF THE INVENTION

1. Field of the Invention

The present invention relates to fluorescent latices exhibiting high quantum yields, very low detection thresholds for fluorescence and the constituent particulates of which incorporate at least one hydrophobic fluorochrome.

2. Description of the Prior Art

Latices are known to this art as aqueous dispersions of polymer particles, the size of which generally ranges from 0.1 microns to several microns. Taking account of their particulate nature, latices have a high specific surface which is exploited to advantage in a wide variety of applications and, in particular, in the paint, magnetic tape and recording industries and in various fields of biology.

In biology and more particularly in the field of immunology, conventional techniques for quantitative determinations employ latices as a support for markers of the enzyme or radioisotope type to permit the quantitative determination of the species present in the mixtures to be analyzed.

This technique of quantitative determination by molecular labelling using a radioactive isotope is extremely precise and reliable and has a high qualitative sensitivity. However, it has several disadvantages associated with the dispersion of the radioactive sources, prolonged exposure of the personnel, variation with time of the emission of the source relative to the half-life of the element, and most importantly, to the necessity, upon completion of the analysis, to isolate the free reactants from the complexed reactants. Radioactive emission is, in effect, completely insensitive to the environment of the label.

For the reasons given above, the technique of analysis by fluorescence represents the most efficient alternative for the replacement of these conventional labels.

The advantages of fluorescent labelling, in comparison with radioactive labelling, are manifold. The risk of radioactive exposure is zero. Fluorescent labelling exhibits an excellent stability with time and, significantly, it provides a more refined response due to the specificity of fluorescent emission to certain environmental parameters. Thus, its use does not require post-analysis separations.

The practical use of fluorescence, in immunological quantitative determinations, thus remains simply subordinated to a demand for quantitative sensitivity. Its sensitivity must be comparable with that of radioactive labelling which entails operating at concentrations ranging from $10^{-12}$ to $10^{-15}$ mol of particles per liter.

Currently, it is the level of its sensitivity that limits the use of analytical techniques based on fluorescence.

Fluorescence, resulting from simple molecular grafting, exhibits insufficient sensitivity for the purpose of a generalized practical application. It is difficult to detect same when the concentration of the entities present in the medium of analysis is less than $10^{-9}$ mol/liter.

SUMMARY OF THE INVENTION

Accordingly, a major object of the present invention is the provision of improved fluorescent latices comprising an encapsulated fluorochrome which are well suited for a wide variety of analytical techniques, the chemical nature of said fluorochrome and the degree of the occupation thereof in the particles of the latex providing a high quantum yield and a very low detection threshold for fluorescence.

Another object of the present invention is the provision of improved fluorescent latices presenting the advantage of comprising particles whose external surface area remains sufficiently free to permit adsorption and, optionally, subsequent grafting thereto of biological active agents.

Briefly, the present invention features fluorescent latices, the particles of which contain at least one encapsulated hydrophobic fluorochrome, having a detection threshold for fluorescence which is less than or equal to $10^{-12}$ mol of particles per liter of latex and said hydrophobic fluorochrome, encapsulated in the particles of the latex, notably comprising a condensed polyaromatic compound or substituted derivative thereof, or a tetraphenylporphine and/or one of the organometallic complexes of same.

DETAILED DESCRIPTION OF BEST MODE AND PREFERRED EMBODIMENTS OF THE INVENTION

More particularly according to the present invention, by the term "encapsulated" is intended that the fluorochromes are virtually absent from the face surfaces of the particles. They are principally concentrated inside the monomer particles such as to maintain available the external surface area thereof.

The fluorochromes according to the invention are selected such as to circumscribe, in emission, the four major regions of the visible spectrum, namely, the blue (400–500 nm), the green (500–550 nm), the yellow (550–600 nm) and the red (600–750 nm).

Other than the required spectral properties, these fluorochromes also satisfy the following requirements:

(a) They are hydrophobic such as to promote their insertion into the latex particles and to preclude any subsequent release thereof;

(b) They exhibit an affinity for the inside or internal volume of the particle, i.e., are chemically compatible with the polymer constituting the latex particles and, if appropriate, with the chemical functional groups present on this polymer. This compatibility plays a crucial role during the synthesis of the corresponding fluorescent latex;

(c) Finally, taking account of their use in immunology, these fluorochromes are chemically and photochemically stable.

The preferred fluorochromes comprise at least five conjugated aromatic ring members, at least three of said aromatic nuclei being condensed.

Too, the condensed moiety of the subject fluorochromes may be substituted by one to five aromatic rings via a single chemical bond, a methylene radical, or one to three conjugated double bonds.

The subject fluorochromes may optionally be substituted by one or more halogen atoms, preferably from one to four halogen atoms. Also preferably, the subject fluorochromes comprise from five to ten aromatic ring members.

In another embodiment of the invention, the subject fluorochromes comprise a tetraphenylporphine or organometallic complex thereof.

Among the fluorochromes which are suitable for the invention, particularly representative are 9,10-diphenylanthracenes (9,10-DPA), 9,10-bis(phenylethynyl) anthracenes (9,10-BPEA), 1,8-dichloro-9,10-bis(phenylethynyl)anthracenes (1,8-Cl$_2$-9,10-BPEA), 5,12-bis(phenylethynyl) naphthacenes (5,12-BPEN), 6,13-bis(phenylethynyl)pentacenes, tetrabenzo[de,hi,op,st] pentacenes, the substituted derivatives thereof, tetraphenylporphine and zinc tetraphenylporphine.

Generally, the fluorochromes are selected as a function of the purpose and the conditions of use of the latex particles.

9,10-Bis(phenylethynyl)anthracenes emit at wavelengths ranging from 480 to 550 nm, i.e., in the green region. These molecules are strongly emitting and have quantum yields close to one. Exemplary of the substituted derivatives of BPEA, emitting in the same wavelengths, are, in particular, 2-ethyl-9,10-BPEA, 1-chloro-9,10-BPEA, 2-chloro-9,10-BPEA, 1,4-dimethyl-9,10BPEA, 1-phenyl-9,10-BPEA and 1,4-diphenyl-9,10-BPEA.

5,12-Bis(phenylethynyl)naphthacenes(5,12BPEN), as well as 1,8-dichloro-9,10-BPEA, emit at wavelengths ranging from 560 to 650 nm.

In respect of tetraphenylporphine, zinc tetraphenylporphine, 6,13-bis(phenylethynyl)pentacene or tetrabenzo[de,hi,op,st]pentacene, these emit at red light wavelengths.

The aforesaid fluorochromes present several advantages:

Such fluorochromes are commercially available and are inexpensive. They are insoluble in water and are chemically and photochemically stable. Being compatible with the polymers of the latex, they provide, upon incorporation thereof in the latex particulates, labels exhibiting an unexpected sensitivity which is markedly more enhanced than those of the conventional labels.

The latex particles containing said fluorochromes conventionally comprise polymers prepared by polymerization of ethylenically unsaturated monomers. Characteristically, these are homopolymers or copolymers containing recurring structural units derived from vinyl aromatic or olefinic monomers or from alkanoic or ethylenic acids or esters, optionally functionalized.

These polymers are readily available and can easily be prepared. Typical such polymers are prepared from:

(i) ethylenic monomers of isoprene, 1,3-butadiene, vinylidene chloride or acrylonitrile type, (ii) vinyl aromatic monomers, such as styrene, bromostyrene, alpha-methylstyrene, ethylstyrene, vinyltoluene, chlorostyrene or chloromethylstyrene or vinylnaphthalene, (iii) alkanoic acids, esters or anhydrides, such as acrylic or methacrylic acids or alkyl acrylates and methacrylates, the alkyl moiety of which has from 3 to 10 carbon atoms, hydroxyacrylates or the esters of ethylenic acids having 4 or 5 carbon atoms, and, (iv) the copolymers of these monomers with each other, such as divinylbenzene or 2,2-dimethyl-1,3-propylene diacrylate and/or with other water-insoluble comonomers copolymerizable therewith.

The monomers can be substituted by anionic or cationic groups of sulfate, sulfonate, phosphonate or quaternary ammonium type. They can also be substituted by groups that react, directly or indirectly, with functional groups of amine type, for example, borne by biological molecules or active agents, such as proteins and enzymes. Representatives of these functional groups are the halogens, carboxyl, amine, isocyanate, aziridine, aldehyde or sulfonyl groups and epoxy functional groups.

The more preferred monomers are of the arylene and/or alkylene families. These are preferably vinyl aromatic compounds, such as styrene, alpha-methylstyrene, ethylstyrene, tert-butylstyrene and vinyltoluene. Preferably, these monomers are substituted by one or more functional groups of halogen, amine, alkoxy, carboxyl and/or sulfonyl type.

These monomers are used alone or in admixture with each other in any proportion, or else as a mixture with another copolymerizable monomer selected from among those indicated above.

The polymer particles can be prepared via polymerization technique, such as conventional emulsion polymerization, microemulsion polymerization or, if appropriate, by polymerization in an organic medium. These techniques are all well known to this art.

The particles, constituting a fluorescent latex according to the invention, are hydrophobic and preferably have a size generally ranging from 0.01 micron to 20 microns and preferably less than 5 microns. They are graded, monodispersed and present in the latex at a concentration of an amount ranging from 0.2 to 50% by weight of the total weight of the latex.

The present invention also features a process for the preparation of the subject fluorescent latices.

The fluorescent labelling is carried out by insertion of the selected fluorochromes into the particles, via techniques known to the art as overpolymerization or solvent swelling.

More particularly, the present invention features a process for preparing a fluorescent latex which comprises a step of: (i) introducing, during polymerization of the monomer(s) constituting the latex particles, a fluorochrome in suspension in a fraction of the monomer or one of the monomers and compatible with water, or (ii) mixing a hydrophobic fluorochrome, solubilized in a water-compatible non-aqueous solvent, with an aqueous dispersion of latex particles, wherein said fluorochrome is selected from among the condensed polyaromatics or substituted derivatives thereof, tetraphenylporphine or the organometallic complexes thereof, and, at the end of the reaction, a latex is produced having a detection threshold for fluorescence which is less than $10^{-12}$ mol of particles per liter of latex.

The overpolymerization technique entails a synthesis of "core/shell" type. A latex seed is overpolymerized by a monomer in the presence of the initiator and of a surface-active agent. The fluorochrome, in suspension in a fraction of this monomer, is introduced at the end of polymerization such as to obtain latex beads, of a precise and narrow particle size, in which the fluorochrome is encapsulated at a more or less great distance from the core of the particles. After polymerization, the latex is "stripped" in order to remove all trace of residual monomers and then purified.

According to the solvent swelling method, the latex particles, in the form of an aqueous dispersion, are contacted with the hydrophobic fluorochrome solubilized in a solvent which is non-aqueous and capable of swelling said particles. This absorption is preferably carried out while raising the temperature. The temperature increase, combined with the presence of solvent, is such that it can be above the glass transition temperatures of the constituent polymer of the particles. The macromolecular polymer chains thus acquire sufficient mobility to permit entry of the fluorochrome, which is very hydrophobic. The value of this temperature, of course, depends on the characteristics of the polymer constituting the particles and on the affinity of the fluorochrome for the latter. Generally, it ranges from 30° C. to 95° C.

The addition of the fluorochrome solution is controlled over time to avoid any precipitation of the hydrophobic compound in the aqueous solution and also the formation of agglomerates of polymer particles.

At the end of a certain period of time, the organic solvent is removed by slow distillation which effects the precipitation of the fluorochrome within the latex particles. The fluorescent latex particles are then purified according to conventional purification techniques.

The water-immiscible solvents are preferably selected from among acetone, chloroform, dichloromethane, cyclohexanone, xylene and toluene.

The fluorescent latex particles, prepared via one or the other of the aforesaid two methods, are then characterized in terms of "degree of occupation" in fluorochromes, of residual fluorescence and of detection sensitivity for the emission of fluorescence.

The maximum degree of occupation of the latex particles in respect of the hydrophobic fluorochromes depends, of course, on the nature of the fluorochrome, on the insertion technique employed, on the nature of the polymer constituting the particles and on the size of these particles. However, this degree has a value such that the fluorescence detection threshold is at most $10^{-12}$, preferably ranging from $10^{-12}$ to $10^{-18}$, mol of particles per liter of latex.

This degree of occupation can thus widely vary and attains values of several millions of molecules of fluorochromes per latex particles.

For example, for a particle having a diameter of 0.5 µm, this degree ranges from 10,000 to 400,000, preferably from 60,000 to 350,000, molecules of fluorochromes per latex particle.

The fluorescent latex particles may also be characterized in terms of concentration per dry weight (or dry solids content) of latex.

The concentration of fluorochromes generally ranges from 0.1% to 10% by weight with respect to the dry weight of the latex. Preferably, this concentration is less than 5% and more preferably ranges from 0.2% to 2%.

The incorporation of the fluorochromes within the particles, according to one or the other of the two techniques indicated above, presents the following advantages:

(1) It prevents release of the fluorochrome during quantitative determination. No so-called residual fluorescence phenomenon is observed in the supernatant. The result is an increased reliability of the quantitative determination technique;

(2) The external surface area of the latex particles remains available for chemical or biological coupling thereto.

In one specific embodiment of the invention, the fluorescent latex is additionally functionalized by at least one immunoreactive species.

Generally, the coupling of a fluorescent latex to an immunoreactive species is carried out by means of one or more reactive functional group(s) present at the surface of these particles.

The conventional procedure for carrying out this type of coupling entails the creation of a covalent bond with this immunoreactive species, by simple chemical reaction. The chemical groups, present at the surface of the particles, can either react directly with the immunoreactive compounds which bear free amine or thiol functional groups, or indirectly after activation. Exemplary functional groups include, in particular, the carboxyl, haloalkyl, alkanesulfonyl and vinylsulfonyl groups. In the event of aldehyde and epoxy groups, these can be activated chemically beforehand to provide a functional group exhibiting a greater activity with respect to immunoreactive species.

By the term "immunoreactive species" is intended any chemical or biological compound bearing at least one site capable of complexing to another specific molecule, designated the receptor. Exemplary immunoreactive species include the primary amines, amino acids, peptides, proteins, lipoproteins or microorganisms of virus or bacteria type, etc. It can also be an antibody or an enzyme. Such immunoreactive species serves the essential function of reacting with another species, either by simple biological affinity or by chemical reaction, by complexing via one of its functional groups to a receptor site for the species to be quantitatively determined.

The addition of these immunoreactive species to the fluorescent latex particles is carried out via conventional technique, using known reactions well known to this art.

The fluorescent latices according to the invention are more particularly intended to be used directly or indirectly in biological analyses. They can, for example, be used as reactants in immunological tests, as scintillators, as calibration standards in flow cytofluorometry, for example, or even as cell labels. In the latter case, particles of a fluorescent latex are phagocytosed by the cells to be studied.

More particularly respecting the immunological quantitative determinations, these preferably employ fluorescent latexes according to the invention additionally functionalized by at least one immunoreactive species.

A significant advantage of fluorescence over other techniques, such as UV/visible or radioactive emission, is to additionally permit the quantitative determination of inhibiting compounds. This characteristic enables the fluorescent latexes according to the invention to be used for such additional practical applications as the quantitative determinations of trace amounts of heavy metals, of oxygen, and the like. This technique is the subject of applications in immunology. More particularly, it concerns the reverse immunofluorescence technique.

In order to further illustrate the present invention and the advantages thereof, the following specific examples are given, it being understood that same are intended only as illustrative and in nowise limitative.

In said examples to follow, the fluorescent latexes were characterized by their detection threshold of fluorescent emission and, as regards their respective particles, by their degree of occupation in fluorochromes via the following techniques:

(A) Measurement of the Detection Threshold of Fluorescence

This entailed determining the minimum concentration of particles detectable by a fluorimeter under acceptable conditions as regards the signal/noise ratio (>10), by means of a conventional fluorimeter and without deoxygenation of the medium. This conventional fluorimeter comprised a polychromatic light source (Xenon 150 W lamp), grating monochromaters, a conventional guide and a device for reading and/or recording the induced photocurrent. It did not also contain any specific device for treating the signal. It is clear that this minimum detectable concentration depended strongly on the conditions of analysis.

Consequently, the values reported in the examples below, determined under standard conditions, must be regarded as indicative of the minimum results of the fluorescent latices analyzed.

To accomplish this, a study of the intensity emitted as a function of the dilution of the starting latex was carried out at precise excitation and emission wavelengths and for optical or electronic parameters of the fluorimeter defined and fixed beforehand.

For purposes of indication, the determinations of the detection thresholds presented below were carried out using the following lasers:

(a) Helium/Neon laser (HeNe): 543, 633 nm (593, 612)

(b) Ionized Argon/Argon laser: 458, 488 and 515 nm (main lines).

The value of the minimum concentration was then deduced by reading the corresponding intensity/concentration curve.

(B) Determination of the Degree of Occupation of a Particle in Fluorochromes

This degree was determined by dissolving a known weight of dry latex in a solvent common to the polymer and to the fluorochrome. Typically, it was toluene. The concentration of fluorochrome was then determined by UV/visible absorption. The concentration of particles was calculated from the weight of dry polymer, from the size of the particles and from the density of the polymer.

The degree of occupation $\eta_p$ was then provided by the ratio:

$$\eta_p = \frac{\text{concentration of fluorochrome}}{\text{concentration of particles}}$$

EXAMPLE 1

Formulation of a Fluorescent Latex Using Tetraphenylporphine

This fluorescent latex was prepared according to the swelling technique, using the following reactants:

(i) Estapor K$_1$030 batch 326®latex 130 g at 7.75%, (carboxylated polystyrene latex of μ=0.3 μ),
(ii) Toluene 20 g,
(iii) Acetone 80 g,
(iv) Tetraphenylporphine 80 mg,
(v) Potassium laurate 0.3 g dry,
(vi) 20% NH$_4$OH qs for pH 10.

Procedure

The tetraphenylporphine was dissolved in the toluene and then the acetone was added. The pH of the latex was adjusted with NH$_4$OH to a value of 10. The potassium laurate was then added to the latex and the total mixture was homogenized for a few minutes with stirring.

The fluorochrome solution was then added slowly to the latex. The resulting suspension was stirred for 3 hours at 40° C. The organic solvents were then removed by distilling as slowly as possible. The fluorescent latex thus obtained was washed by ultrafiltration.

Characteristics of the Fluorescent Latex (a) Diameter of the particles 0,293 μm.
(b) Absence of fluorochrome in serum (measurement of the fluorescence of the ultrafiltrate).
(c) The mean degree of occupation was 60,000 molecules of TPP per latex particle.
(d) The fluorescence of the latex was stable under irradiation and comparable with that of a solution of TPP in toluene:

$\lambda_{ex}$=420 nm (strong), 515 nm and 550 nm (weak), $\lambda_{em}$=656 nm and 720 nm (720/656 ratio=0.3).

(e) The detection threshold of fluorescence was $2\times10^{-13}$ mol of particles per liter of latex, which indicates a very high detection sensitivity.

EXAMPLE 2

Formulation of a Fluorescent Latex Using 5,12-bis(phenylethynyl)naphthacene(5,12-BPEN)

This latex was formulated in accordance with the procedure described in Example 1, using the following reactants:

| (i) | Estapor K$_1$030 batch 326 ® latex 65 g at 7.75%, (carboxylated polystyrene latex of φ 0.3 μ), | |
|---|---|---|
| (ii) | 5,12-BPEN | 40 mg, |
| (iii) | Acetone | 60 g, |
| (iv) | Toluene | 10 g, |
| (v) | Potassium laurate | 0.3 g dry, |
| (vi) | 20% NH$_4$OH qs for pH 10. | |

In this procedure, the swelling was carried out over 3 hours at 50° C. After distillation, the latex was washed by ultrafiltration and characterized.

Characteristics of the fluorescent latex (a) Diameter of the particles: 0.293 μm,
(b) The mean degree of occupation of the particles was 125,000 molecules of fluorochrome per latex particle.
(c) The fluorescence was stable under exciting irradiation.
(d) The maximum excitation was at 565 nm but a strong emission could be obtained by excitation with the He/Ne laser at 543 nm (80%) or with the ionized Argon laser at 515 nm (80%).

| Emission: | 568 nm (maximum) |
|---|---|
| | 610 nm (610/563 = 0.3) |

(e) The detection threshold was very low, in the vicinity of about $4\times10^{-15}$ mol of particles per liter of latex. The sensitivity of the fluorescent latex was therefore excellent.

EXAMPLE 3

Formulation of a Fluorescent Latex Using 5,12-bis(phenylethynyl)naphthacene(5.12-BPEN)

This latex was obtained in accordance with the procedure described in Example 1, using the following reactants:

| (i) | Estapor K$_1$010 batch 786 ® latex 79.7 g at 12.54%, (carboxylated polystyrene latex of φ = 0.1 μ), | |
|---|---|---|
| (ii) | 5,12-BPEN, | 78 mg, |
| (iii) | Acetone | 222 g, |
| (iv) | Toluene | 14.5 g. |

The fluorochrome was dissolved in 122 g of acetone and 14.5 g of toluene. This was maintained under stirring for 12 hours. In parallel, 100 g of acetone were incorporated into the latex. The two mixtures were then combined.

Swelling was carried out at 50° C. for 3 hours. After distillation, the latex was washed by ultrafiltration and characterized.

Characteristics of the Fluorescent Latex (a) Diameter of the particles: 0.185 μm.
(b) The mean degree of occupation of the particles was 30,000 molecules of fluorochrome per latex particle.
(c) The fluorescence of the latex was strong:

$\lambda_{ex}$=515 nm, 555 nm, $\lambda_{em}$=568 nm, 610 nm.

(d) The detection threshold was in the vicinity of about $2\times10^{-14}$ mol of particles per liter of latex.

EXAMPLE 4

Formulation of a Fluorescent Latex Using 9,10-bis(phenylethynyl)anthracene(9,10-BPEA)

This latex was formulated in accordance with the procedure described in Example 1, using the following reactants:

| (i) | Estapor K₁080 batch 705 ® latex 17 g at 29.4% (carboxylated polystyrene latex of ϕ = 0.9 μm), | |
|---|---|---|
| (ii) | 9,10-BPEA | 22 mg, |
| (iii) | Acetone | 49 g, |
| (iv) | Cyclohexanone | 5 g. |

In this procedure, the swelling was carried out over 3 hours at 50° C. After distillation, the latex was washed by ultrafiltration and characterized.

Characteristics of the Fluorescent Latex (a) Diameter of the particles: 0.899 μm (b) The mean degree of occupation of the particles was $2.9 \times 10^6$ molecules of fluorochrome per latex particle.

(c) The fluorescence of the latex was strong:

$\lambda_{ex}$=440 nm, 455 nm, 468 nm (strong)

λem=480 nm (strong), 510 nm (d) The detection threshold was very low, since it was in the vicinity of about $7 \times 10^{-17}$ mol of particles per liter of latex. The sensitivity of the fluorescent latex was therefore excellent.

EXAMPLE 5

Formulation of a Fluorescent Latex Using 1,8-dichloro-9,10-bis(phenylethynyl)anthracene (1,8-Cl₂-9,10-BPEA)

This latex was formulated in accordance with the procedure described in Example 1, using the following reactants:

| (i) | Estapor K₁080 batch 326 ® latex 65 g at 8.13% (carboxylated polystyrene latex of ϕ = 0.3 μm), | |
|---|---|---|
| (ii) | 1,8-Cl₂-9,10-BPEA | 55 mg, |
| (iii) | Acetone | 98 g, |
| (iv) | Toluene | 7.5 g, |
| (v) | Potassium laurate | 0.05 g, |
| (vi) | 20% NH₄OH qs for pH 10. | |

In this procedure, the swelling was carried out over 3 hours at 50° C. After distillation, the latex was washed by ultrafiltration and characterized.

Characteristics of the Fluorescent Latex (a) Diameter of the particles: 0.328 μm, (b) Mean degree of occupation of the particles was 276,000 molecules of fluorochrome per latex particle.

(c) The fluorescence of the latex was intense:

$\lambda_{ex}$=470 nm (main), 490 nm $\lambda_{em}$=525 nm (main), 560 nm (d) The detection threshold was very low, in the vicinity of about $1.5 \times 10^{-15}$ particles per liter of latex. The sensitivity of the fluorescent latex was therefore excellent.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Fluorescent latex particulates, comprising:

polymer particles having at least one hydrophobic fluorochrome encapsulated therein, wherein said hydrophobic fluorochrome comprises at least five conjugated aromatic ring members wherein at least three of the aromatic rings are condensed, a tetraphenylporphine or an organometallic complex thereof; wherein the external face surfaces of said polymer particles are essentially devoid of said hydrophobic fluorochrome; wherein said particulates have a detection threshold for fluorescence which is less than or equal to $10^{-12}$ mol of particles per liter of latex; and the concentration of said hydrophobic fluorochrome ranges from 0.1% to 2% on the basis of dry weight of latex.

2. The fluorescent latex particulates of claim 1, wherein said concentration of said hydrophobic fluorochrome ranges from 0.1% to 1.04% on the basis of dry weight of latex.

3. The fluorescent latex particulates of claim 1, wherein said polymer particle has encapsulated therein a mixture of a tetraphenylporphine and an organometallic complex thereof.

4. The fluorescent latex particulates of claim 1, wherein, said at least one hydrophobic fluorochrome is 9,10-diphenylanthracene, 9,10-bis(phenylethynyl)anthracene, 1,8-dichloro-9,10-bis(phenylethynyl)anthracene, 5,12-bis(phenylethynyl) pentacene, tetrabenzo[de,hi,op,st]pentacene, tetraphenylporphine or zinc tetraphenylporphine.

5. The fluorescent latex particulates of claim 1, wherein the particulates have a particle size ranging from 0.01 microns to 20 microns.

6. The fluorescent latex particulates of claim 1, wherein the particulates have a particle size less than 5 microns.

7. The fluorescent latex particulates of claim 1, wherein the particulates have a detection threshold for fluorescence ranging from $10^{-12}$ to $10^{-}$mol of particles per liter of latex.

8. The fluorescent latex particulates of claim 1, wherein said polymer particles comprise the (co)polymerizate of an ethylenically unsaturated or vinyl aromatic (co)monomer; or of an alkanoic acid, ester or anhydride.

9. The fluorescent latex particulates of claim 1, wherein said hydrophobic fluorochrome is substituted by one to five aromatic ring members via a single chemical bond, a methylene radical, or one to three conjugated double bonds.

10. The fluorescent latex particulates of claim 1, wherein said hydrophobic fluorochrome is substituted by one or more halogen atoms.

11. The fluorescent latex particulates of claim 1, wherein said hydrophobic fluorochrome is substituted by one to four halogen atoms.

12. The fluorescent latex particulates of claim 1, wherein said hydrophobic fluorochrome comprises from 5 to 10 aromatic nuclei.

13. The fluorescent latex particulates of claim 1, wherein said polymer particles have at least one immunoreactive species coupled to the external face surfaces thereof.

14. The fluorescent latex particulates of claim 13, wherein said at least one immunoreactive species s covalently bonded to said external face surfaces of said polymer particles.

15. The fluorescent latex particles of claim 13, wherein said at least one immunoreactive species is capable of binding to at least one receptor molecule.

16. A latex comprising the fluorescent latex particulates of claim 1.

17. A latex comprising the fluorescent latex particulates of claim 5.

18. A latex comprising the fluorescent latex particulates of claim 8.

19. A latex comprising the fluorescent latex particulates of claim 13.

20. The latex of claim 16, wherein said polymer particles comprise from 0.2% to 50% by weight of said latex.

21. A process for the preparation of the latex of claim 16, comprising polymerizing, in an aqueous medium, least one monomer in the presence of a suspension of said at least one fluorochrome.

22. A process for the preparation of the latex of claim 16, comprising intimately admixing said at least one fluorochrome, solubilized in a non-aqueous solvent therefor, with an aqueous dispersion of said polymer particles.

23. In an immunological analytical technique, a reverse immuno-fluorescence analytical technique, a scintillator analytical technique, a calibration standard technique or a cell labelling technique, wherein said technique employs a fluorescent reactant, wherein the improvement comprises employing as said fluorescent reactant, the fluorescent latex of claim 16.

* * * * *